(12) United States Patent
Lee et al.

(10) Patent No.: US 8,741,632 B2
(45) Date of Patent: Jun. 3, 2014

(54) ONE-STEP METHOD FOR PRETREATING BIOMASS USING NANOMIXING

(75) Inventors: Ilsoon Lee, Okemos, MI (US); Wei Wang, Lansing, MI (US); Shaowen Ji, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 138 days.

(21) Appl. No.: 13/194,689

(22) Filed: Jul. 29, 2011

(65) Prior Publication Data

US 2012/0036765 A1  Feb. 16, 2012

Related U.S. Application Data

(60) Provisional application No. 61/372,268, filed on Aug. 10, 2010.

(51) Int. Cl.
*C12P 5/00*   (2006.01)
*C12P 19/44*  (2006.01)
*C12P 7/62*   (2006.01)
*C10L 1/19*   (2006.01)
*C10L 1/02*   (2006.01)

(52) U.S. Cl.
USPC .................... 435/289.1; 435/132; 44/307

(58) Field of Classification Search
USPC .............................. 435/132, 289.1
See application file for complete search history.

(56) References Cited

U.S. PATENT DOCUMENTS 5,498,766 A * 3/1996 Stuart et al. ............. 435/99
8,148,559 B1   4/2012 Walker et al.
2008/0227182 A1 * 9/2008 Anderson et al. ........ 435/267
2011/0081689 A1   4/2011 Flanegan et al.
2012/0036765 A1   2/2012 Lee et al.

FOREIGN PATENT DOCUMENTS

WO   WO 2009156464 A2 * 12/2009

OTHER PUBLICATIONS

Supraton by Krupp (product in use in 1996 per Stuart reference).*
Dispax devices by Ika Works (product in use since 1996 per Stuart reference).*
Cheng, Gang et al. "Transition of Cellulose Crystalline Structure and Surface Morphology of Biomass as a Function of Ionic Liquid Pretreatment and Its Relation to Enzymatic Hydrolysis" Biomacromolecules 2011, 12, 933-941.
Dadi, A. P, et al., "Enhancement of cellulose saccharification kinetics using an ionic liquid pretreatment step", Biotechnol Bioeng., 95(5), (Dec. 5, 2006), 904-10.
Lee, S. H, et al., "Ionic liquid-mediated selective extraction of lignin from wood leading to enhanced enzymatic cellulose hydrolysis", Biotechnol Bioeng., 102(5), (Apr. 1, 2009), 1368-76.
Mosier, Nathan, et al., "Features of promising technologies for pretreatment of lignocellulosic biomass", Bioresource Technology, (Apr. 2005), 673-86.

(Continued)

*Primary Examiner* — Pamela H Weiss
(74) *Attorney, Agent, or Firm* — Clark IP Law, PLC

(57) ABSTRACT

Methods and devices for treatment of biomass comprised of crystalline structures are described that provide a combined mechanical, chemical and thermal effect (i.e., nano-hybrid pretreatment) to synergistically break down the crystalline structures. Such nano-hybrid mixing provides efficient, and cost-effective breakdown which enhances enzymatic accessibility to lignocellulosic materials. Methods and devices shown can be used to produce products such as pulp, chemicals, or biofuels.

28 Claims, 12 Drawing Sheets

(56) References Cited

OTHER PUBLICATIONS

Byrd et al., "Simplified Pulping & Bleaching of Corn Stalks", Department of Wood & Paper Science, North Carolina State University, Raleigh, NC, 2005, 50 pages.

Chen et al., "Comparison of Four Different Chemical Pretreatments of Corn Stover for Enhancing Enzymatic Digestibility", Biomass and Bioenergy, vol. 33, No. 10, Elsevier Ltd., Oct. 2009, pp. 1381-1385.

JI et al., "Impact of Cationic Polyelectrolyte on the Nanoshear Hybrid Alkaline Pretreatment of Corn Stover: Morphology and Saccharification Study", Bioresource Technology, vol. 133, 2013, pp. 45-50.

Larson et al., "A Cost-Benefit Assessment of Gasification-Based Biorefining in the Kraft Pulp and Paper Industry", Final Report, Under contract DE-FG26-04NT42260 with the U.S. Department of Energy and with cost-sharing by the American Forest and Paper Association, Dec. 2006, 365 pages.

Lu et al., "Carbon Nanotunes Tuned Foam Structures as Novel Nanostructured Biocarriers for Lignocellulose Hydrolysis", Biotechnology Letters, vol. 35, No. 2, 2013, pp. 181-188.

Lu et al., "Enzyme Production by the Mixed Fungal Culture With Nano-Shear Prettreated Biomass and Lignocellulose Hydrolysis", Biotechnology and Bioengineering, vol. 110, No. 8, Aug. 2013, pp. 2123-2130.

Purevision Technology, Inc., "The Fractionation of Loblolly Pine Woodchips into Pulp Used for Making Paper Products", Final Technical Report, DoE award number. DE-FG36-05GO15154, 2006, 11 pages.

The National Renewable Energy, Laboratory, "Modeling Tomorrow's Biorefinery—the NREL Biochemical Pilot Plant", Biomass Program, U.S. Department of Energy, Energy Efficiency and Renewable Energy, 2008, 4 pages.

The Pacific Northwest National, Laboratory et al., "Top Value Added Chemicals From Biomass, Volume I: Results of Screening for Potential Candidates from Sugars and Synthesis Gas", Biomass, U.S. Department of Energy, Energy Efficiency and Renewable Energy, Aug. 2004, 76 pages.

The Pacific Northwest National, Laboratory et al., "Top Value Added Chemicals From Biomass, Volume II: Results of Screening for Potential Candidates from Sugars and Synthesis Gas", Biomass, U.S. Department of Energy, Energy Efficiency and Renewable Energy, Oct. 2007, 87 pages.

Tschirner et al., "Recycling of Chemical Pulp from wheat straw and Corn Stover", BioResources, vol. 2, No. 4, 2007, pp. 536-543.

Zhao et al., "Combined Supercritical and Subcritical Process for Cellulose Hydrolysis to Fermentable Hexoses", Environ. Sci, Technol., vol. 43, No. 5, Mar. 2009, pp. 1565-1570.

* cited by examiner

US 8,741,632 B2

ONE-STEP METHOD FOR PRETREATING BIOMASS USING NANOMIXING

This application claims priority under 35 U.S.C. 119(e) to U.S. Provisional Patent Application Ser. No. 61/372,268, filed Aug. 10, 2010, which is hereby incorporated herein by reference in its entirety.

STATEMENT OF GOVERNMENT RIGHTS

This invention was made in part with government support under Grant No. CMMI 0832730 by the National Science Foundation. The government has certain rights in the invention.

BACKGROUND

Treated biomasses are useful in a number of industries. One industry includes pulp production for products such as paper. Another use includes production of biofuels. Alternatives for petroleum are urgently needed since the worldwide oil depletion is approaching. Due to its abundant resources, lignocellulosic biomass such as woody biomass, corn stover and switch grass can be one of the promising candidates for bioethanol production to drastically reduce the dependence of transportation fuels on petroleum, as well as to decrease the green house gas emission.

Bioethanol converted from lignocellulosic biomass is a multistep process, in which pretreatment step accounts for the majority cost portion other than the power plant investment, as high as 19%. Biomass pretreatment refers to a step to disrupt the polysaccharide-lignin shield that limits the accessibility of enzymes to cellulose and hemicellulose, before enzymatic hydrolysis takes place.

SUMMARY

The inventors recognize that effective and efficient pretreatment processes are needed. Accordingly, a method of treating biomass is provided, which comprises combining an amount of biomass containing crystalline structures and an amount of fluid; and nanomixing the biomass and the fluid in a processing chamber to form a biomass slurry, wherein nanomixing degrades the crystalline structures and opens up pores in the crystalline structures. In one embodiment, the pores are no more than about 5 microns in diameter.

In one embodiment, conventional chemical and moderate thermal pretreatment along with in situ nanomixing pretreatment (hereinafter "hybrid nanomixing" or "nano-hybrid pretreatment") is used. Surprisingly, the in situ combination of nanomixing together with chemical and inherent moderate thermal effects provides a synergistic effect to break down the cell wall nanostructures (i.e., crystalline structures) in the biomass. In one embodiment, in situ nanomixing expedites the conventional thermochemical biomass conversion process by up to orders of magnitude faster.

In one embodiment, a method of forming a biofuel is provided, which comprises combining an amount of biomass containing crystalline structures with an amount of fluid in a processing chamber; nanomixing the biomass and the fluid in the chamber to form a biomass slurry (i.e., at least partially breaks the lignin seals), wherein nanomixing degrades the crystalline structures and opens up pores in the crystalline structures; forming glucose from the biomass slurry; and fermenting the glucose to produce a biofuel.

The various embodiments further include products made according to the described processes.

In one embodiment, a biomass treatment device is provided, which comprises a processing chamber; a turbine nanomixer located within the processing chamber; a continuous flow inlet port coupled to the processing chamber, adjacent to the turbine nanomixer; a continuous flow outlet port coupled to the processing chamber, spaced laterally away from the turbine nanomixer; a source of fluid configured for continuous introduction to the processing chamber; a source of biomass configured for introduction at the continuous flow inlet port; and an inline fermenting device to further process material from the continuous flow outlet port.

The various methods and devices described herein provide a continuous, fast, efficient, and cost-effective breakdown which enhances enzymatic accessibility to lignocellulosic materials.

DETAILED DESCRIPTION

Figure 1:
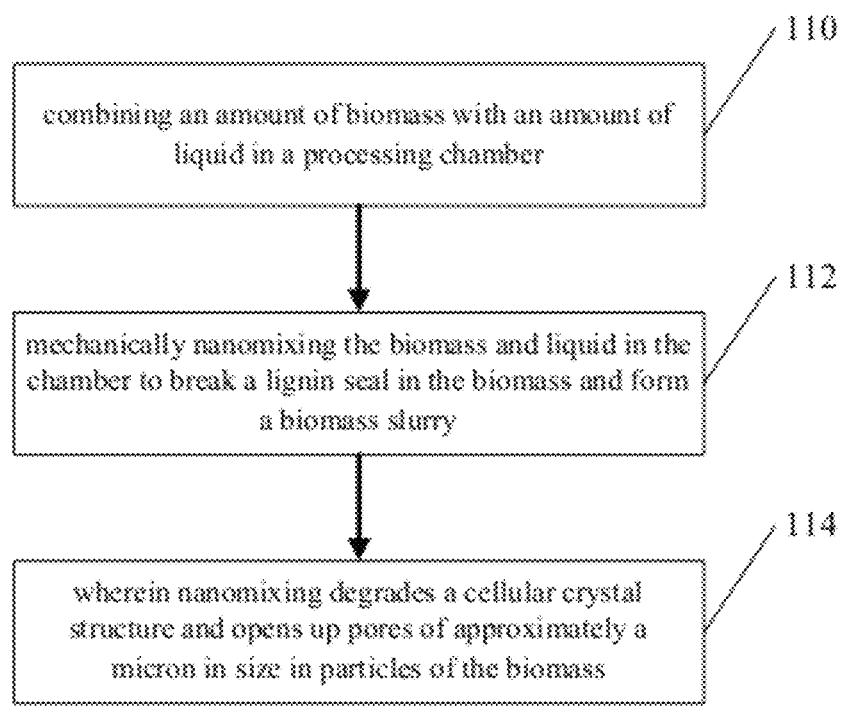
FIG. 1 shows a flow chart of an example method of treating biomass according to an embodiment.

In the following Detailed Description of the invention, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, chemical, and mechanical changes may be made.

The Detailed Description that follows begins with a definition section followed by a description of the embodiments, an example section and a brief conclusion.

DEFINITIONS

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "ligno-cellulosic biomass" as used herein, is intended to refer to virtually any plant-derived organic matter (woody or non-woody) available for energy on a sustainable basis. Plant biomass can include, but is not limited to, agricultural crop wastes and residues such as corn stover, wheat straw, rice straw, sugar cane bagasse, tobacco, and the like. Plant biomass further includes, but is not limited to, various weeds of any type, such as in the Bassicacae family (e.g., *Arabidopsis*), woody energy crops, wood wastes and residues such as trees (e.g., dogwood), further including fruit trees, such as fruit-bearing trees, (e.g., apple trees, orange trees, and the like), softwood forest thinnings, barky wastes, sawdust, paper and pulp industry waste streams, wood fiber, and the like. Additionally grass crops, such as various prairie grasses, including prairie cord grass, switchgrass, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature.

The term "biofuel" as used herein, refers to any renewable solid, liquid or gaseous fuel produced biologically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops (e.g., grains, such as corn), crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step intended to alter native biomass so it can be more efficiently and economically converted to reactive intermediate chemical compounds such as sugars, organic acids, etc., which can then be further processed to a variety of value added products such a value-added chemical, such as ethanol. Pretreatment can reduce the degree of crystallinity of a polymeric substrate, reduce the interference of lignin with biomass conversion and prehydrolyze some of the structural carbohydrates, thus increasing their enzymatic digestibility and accelerating the degradation of biomass to useful products. Pretreatment methods can utilize acids of varying concentrations (including sulfuric acids, hydrochloric acids, organic acids, etc.) and/or other components such as ammonia, ammonium, lime, and the like. Pretreatment methods can additionally or alternatively utilize hydrothermal treatments including water, heat, steam or pressurized steam. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugars.

The term "moisture content" as used herein, refers to percent of water present in the biomass. The moisture content is calculated as grams of water per gram of biomass as received (biomass dry matter plus water) times 100%.

The term "fluid" as used herein, refers to a liquid or gas. The liquid can include a liquid-based solution, which is a liquid further containing one or more additives capable of forming a solution with the liquid. For example, the liquid can include water or a water-based solution One type of liquid-based solution is a base solution which can include, but is not limited to, sodium hydroxide, sodium peroxide, calcium hydroxide, aqueous ammonia, at varying concentrations, further optionally including added oxygen, sulfur dioxide, anthraquinone (AQ) and the like, including combinations thereof. One type of liquid-based solution is an acid solution which can include, but is not limited to, a diluted or non-diluted acid, such as sulfuric acid, hydrochloric acid, nitric acid, and phosphoric acid, and the like, further including combinations thereof.

One type of liquid-based solution can include a solution containing other types of additives which can be either basic or acidic, such as a binding agent or any type of surfactant (e.g., sodium dodecylbenzene sulfonate (SDBS), sodium dodecyl sulfate (SDS), and the like) which can facilitate biomass conversion. Examples of binding agents, include, but are not limited to, phenolic binding agents, such as various types of various polyelectrolytes (e.g., poly(diallyldimethylammonium chloride) (PDAC), sulfonated poly(styrene) (SPS), poly(ethyleimine) (PEI), Poly(acrylic) acid (PAA), Poly(3,4-ethylenedioxythiophene) (PEDT), polyvinylpyrolidone (PVP), and the like). A fluid can further include any type of supercritical fluid or ionic liquid (IL).

The term "nanomixing" is a type of mechanical mixing in a pretreatment process which impacts biomass on a nanoscale level causing at least a portion of a cellular crystal structure (i.e., crystalline structure) to degrade, allowing pores on an order of magnitude of microns in diameter to open.

The term "nanomixer" as used herein, refers to a mechanical device capable of performing nanomixing.

The term "nano-hybrid pretreatment" as used herein, refers to a pretreatment process which includes synergistic in situ combination of nanomixing and conventional thermochemical pretreatments simultaneously in a processing chamber.

The term "nanofibril" as used herein, refers to a nano-sized aggregate of cellulose fibers, in which cellulose linear chains are hydrogen bonded.

The term "cell wall" as used herein, refers to a nanoscale biomass composite structure surrounding the plant cell, mainly containing cellulose, hemicellulose and lignin.

DESCRIPTION OF THE EMBODIMENTS

FIG. 1 shows an example method of treating biomass according to an embodiment. In operation 110, an amount of biomass is combined with an amount of fluid in a processing chamber. The fluid serves to facilitate the biomass conversion process.

Various fluids can be used, as the term is defined herein. In one embodiment, the type and concentration of fluid is chosen so as to minimize fiber degradation. In one embodiment water or various water solutions are used as the fluid. Such solutions can be basic or acidic and further include various types of surfactants and binding agents, such as phenolic binding agents. In one embodiment, the components are added substantially simultaneously. In one embodiment, the components are added sequentially.

In one embodiment, NaOH in varying concentrations is used at as the fluid, such as at least about 0.4% up to about 4%, up to about 10% or higher, such as about 20%, including any range there between, although higher concentrations can cause increased fiber degradation. In one embodiment, at least about two (2) %, such as between about two (2) and about four (4) % of a fluid, such as NaOH is used.

In one embodiment, poly(diallyldimethylammonium chloride) (PDAC) and/or polyvinylpyrolidone (PVP), together with NaOH is used as the fluid. In one embodiment, dilute NaOH and PDAC are used, with the NaOH having a concentration no greater than about 0.4% and the PDAC having a concentration no greater than about 10 mM. In this embodiment, PDAC functions as a surfactant and interacts with lignin and other components to increase enzyme accessibility. Accordingly, use of PDAC has the additional benefit of reducing the amount of expensive enzyme needed.

In one embodiment, a supercritical fluid, such as water or carbon dioxide, is used in a suitable pressure and temperature, such as no more than 300 atm and 500° C.

In one embodiment, an ionic liquid (IL) is used as the fluid. Ionic liquids are also known as liquid electrolytes, ionic melts, ionic fluids, fused salts, liquid salts, or ionic glasses. In general, an ionic liquid is a salt in the liquid state (e.g., a NaCl aqueous solution). In the embodiments contemplated herein, the salts are liquid at or below room temperature. Examples of ionic liquids include, but are not limited to, 1-ethyl-3-methylimidazolium dicyanamide, 1-butyl-3,5-dimethylpyridinium bromide, and the like.

Operation 112 (referred to herein as a 'nano-hybrid' pretreatment or "hybrid nanomixing") comprises, in one embodiment, nanomixing the biomass and fluid in the chamber to break a lignin seal in the biomass and form a biomass slurry. By breaking a lignin seal in the cell walls of the biomass, breakdown of the biomass for subsequent processing steps (e.g., pulp production, sugar production, etc.) is increased. Additionally, subsequent processing steps can benefit from enhanced enzymatic accessibility to the lignocellulosic biomass materials after the lignin seal is broken.

As discussed above, in one embodiment, hybrid nanomixing (i.e., nano-hybrid pretreatment), i.e., a synergistic combination of nanomixing and conventional thermochemical treatment in a chamber simultaneously. Surprisingly, the combination provides a synergistic effect to break down the cell wall structures of the biomass by at least 50% more efficiently as compared with subjecting the biomass to these treatments sequentially.

In one embodiment, nanomixing breaks the lignin seal under conditions that substantially improve the enzymatic accessibility to biomass. Examples of processing conditions that enhance enzymatic accessibility include, but are not limited to, low temperatures (i.e., less than about 100° C.), low pressures (i.e., less than about 2 atm), reduced duration (i.e., less than about one (1) hr) and reduced chemical concentrations (i.e., less than about 20% w/v). In one embodiment, a temperature of less than about 50° C., such as less than about 40° C. or lower is used, down to room temperature conditions. Another example includes temperature less than about 50° C., such as less than about 40° C. and a pressure of about 1 atm. In one embodiment, the process is run under pressure at temperatures which can be less than room temperatures, such as with the use of supercritical fluids as described below.

In one embodiment, the nanomixing occurring during operation 112 degrades crystalline structures (e.g., cellular crystal structure) in the biomass and opens up small pores in the crystalline structures, i.e., crystals. In one embodiment, the pores each have a diameter of less than about 5 microns. Breakdown of the biomass in measurable quantities such as crystallinity, and an increased number of pores having reduced pore dimensions are useful for further biomass processing, such as pulp production or production of biofuels.

Figure 2:
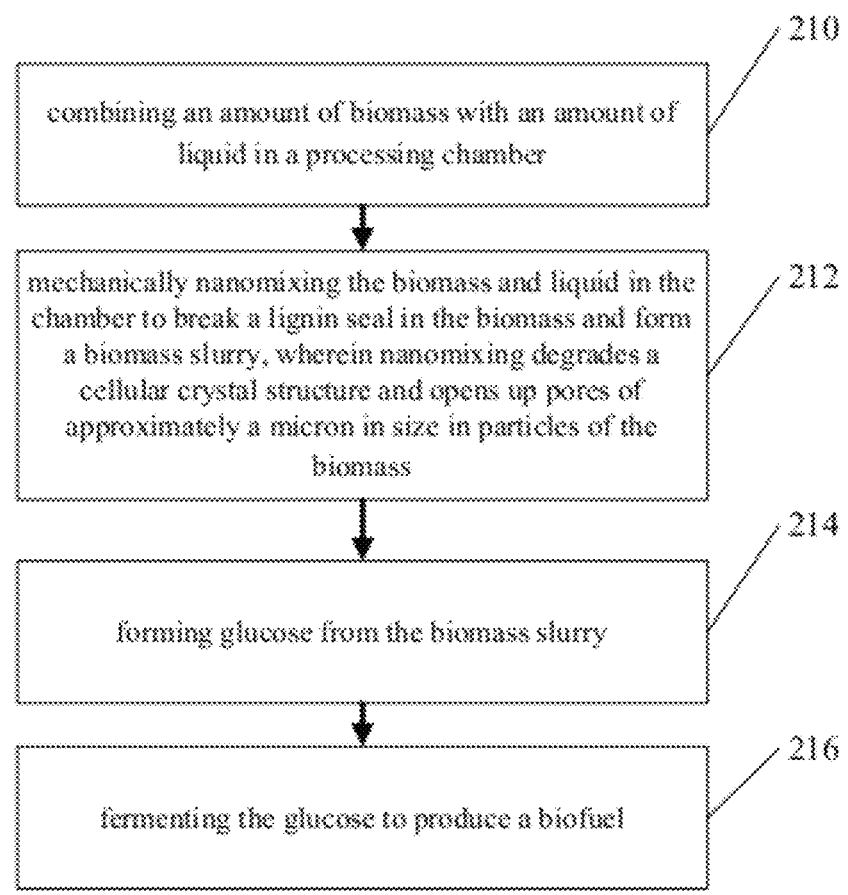
FIG. 2 shows a flow chart of an example method of forming a biofuel according to an embodiment.

FIG. 2 shows one embodiment of a pretreatment method similar to the method described in FIG. 1. Operation 210 comprises, in one embodiment, combining an amount of biomass with an amount of fluid in a processing chamber.

In one example, a supercritical fluid is added as at least a portion of the fluid. In supercritical fluid examples, a pressure of the processing chamber may need to be controlled. In such an example, the processing chamber is sealed to enable control of pressure. Operation 212 (also referred to herein as a 'nano-hybrid' pretreatment) comprises, in one embodiment, nanomixing the biomass and fluid in the chamber to break a lignin seal in the biomass and form a biomass slurry, wherein nanomixing degrades a cellular crystal structure and opens up pores which are on the order of magnitude of micron in size, such as no more than about five (5) microns or less, such as less than about two (2) microns down to about one (1) micron or even about 0.1 microns, including any range there between. In one embodiment, the holes are no greater than about one (1) micron in size, open up in macro-sized fibers (e.g., with sizes ranging from about 10 to about 50 microns) of the biomass. (See also Example Section).

Operation 214 comprises, in one embodiment, forming glucose from the biomass slurry, and operation 216 comprises, in one embodiment, fermenting the glucose to produce a biofuel. While a number of operations in biofuel production are not discussed in the present disclosure, one of ordinary skill in the art, having the benefit of the present disclosure, will recognize that biomass, broken down as described herein, can be further processed into a biofuel or other value-added chemicals such as succinic acid, polymers, and the like.

Figure 3A:
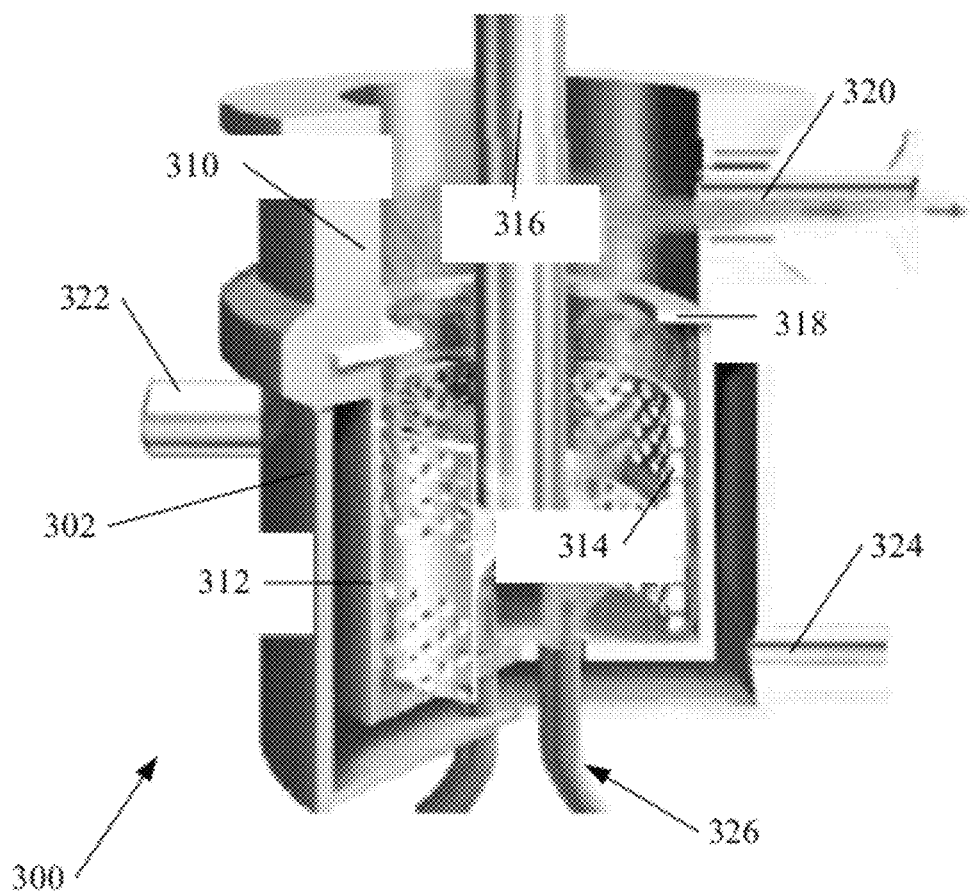
FIG. 3A shows a nanomixer according to an embodiment.

FIG. 3A shows a nanomixer 300 according to an embodiment. A processing chamber 302 is shown. The example processing chamber 302 includes a mixing chamber 312 and an overflow chamber 310. An inlet port 322 is included to introduce mixing components such as biomass or fluid. An outlet port 320 is shown to remove processed biomass slurry. Additional ports 326 are included in selected examples to introduce additional mixing components. In one embodiment, the inlet port 322 and outlet port 320 are configured for continuous flow. Continuous flow is useful for large batch processing, and as discussed below, continuous flow is useful in selected embodiments for process control such as mixing amount.

An example turbine 314 is shown coupled to a drive shaft 316. In one embodiment, a nanomixing operation is performed at mixing speeds in a range between 10 meters per second and 50 meters per second. FIG. 3A shows a cylindrical turbine 314 that produces mixing speeds as a result of rapid spinning of the drive shaft 316. In one embodiment, a turbine configuration of one (1) meter per second mixing speed is produced at the cylindrical shell of the turbine 314. In one embodiment, the turbine 314 is rotated at about 18,000 revolutions per minute. As discussed in more detail below, a number of processing conditions such as mixing speed, temperature, pressure, chemistry of fluid, etc. are combined to achieve increased breakdown of biomass. In various embodiments, a number of processing conditions are combined in synergistic ways to obtain such increased breakdown of biomass.

FIG. 3A also shows an example temperature control port 324 coupled to a portion of the processing chamber 302. In this embodiment, the temperature control port 324 is coupled to the mixing chamber 312. In selected embodiments, the temperature control port 324 is used to flow heating or cooling fluid around the mixing chamber 312 to control processing temperature.

In one embodiment, components, such as biomass and fluid, are introduced to the mixing chamber 312 through the inlet port 322. In one embodiment, high shear speed (e.g., in excess of about 18,000 rpm) is generated by the turbine 314 spinning at a close proximity (e.g., less than about 5 mm) to the walls of the mixing chamber 312. In one embodiment, holes in the turbine 314 on the order of magnitude of millimeters in diameter, such as about (e.g., less than about 1 cm in size and at least about 20 holes) further enhance the uniform spinning of fluid against the wall of the mixing chamber by allowing fluid to flow in a radial direction as well as in a tangential direction. As the mixing components are mixed in the mixing chamber 312, a flow of additional mixing components tends to move already mixed biomass slurry upwards into the overflow chamber 310. Once in the overflow chamber 310, in one embodiment, a rotational momentum further urges the biomass slurry out the outlet port 320.

In one embodiment, a flange 318 is included between the mixing chamber 312 and the overflow chamber 310. The flange 318 can have any suitable shape and size as long as it is capable of performing the desired function of regulating fluid flow. In one embodiment, the flange 318 regulates the amount of time the biomass slurry spends in the mixing chamber 312 before allowing it to move into the overflow chamber 310. Time spent in the mixing chamber 312 relates to an amount of mixing and an amount of breakdown of the biomass. In one embodiment, the process is a batch process with all fluid remaining inside the mixing chamber 312 before being provided to the overflow chamber 310. In one embodiment, the process is a continuous fluid flow operation such that the flange 318 regulates fluid flow by directing a portion of the fluid back into the mixing chamber 312 and a portion to the overflow chamber 310 as new fluid enters an inlet of the mixing chamber 312. In one embodiment, the flange 318 has an end plate capable of causing the desired fluid motion. In one embodiment, the flange further includes a ring-shaped portion. In one embodiment, the flange 318 is tightly fastened to an upper end so that the chamber 312 is closed during processing.

In one embodiment, the biomass slurry is mixed in the mixing chamber 312 for a duration sufficient to cause an effective breakdown to be achieved (i.e., at least 50% lignin is broken down). In one embodiment, the duration is less than about one hour, such as less than about 30 minutes or about 15 minutes or about 10 minutes or less, such as less than about five minutes, down to no more than about two minutes, including any range there between. In one embodiment, the duration is between about 1.5 and 2.5 minutes, such as no more than about 2 minutes. Such reduced durations are up to magnitudes of order shorter than conventional treatments which can require at least one hour of treatment up to 3 or 4 hours or more. (See, for example, Mosier N., et al., *Features of promising technologies for pretreatment of lignocellulosic biomass*, Bioresource Technology 96 (2005) 673-686 (hereinafter "Mosier"), which describes the well-known Kraft paper pulping pretreatment technology).

Figure 3B:
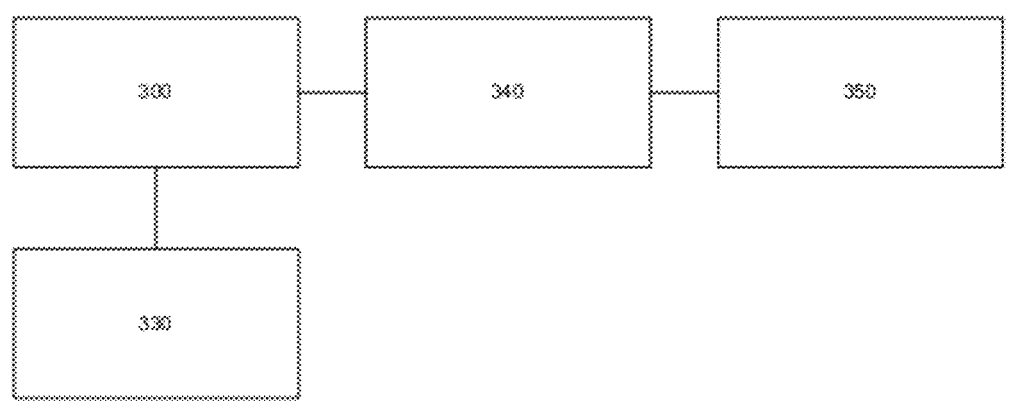
FIG. 3B shows a block diagram of a biomass treatment device according to an embodiment.

FIG. 3B shows a block diagram of a biomass treatment device according to an embodiment. The nanomixer 300 from FIG. 3A is represented in the FIG. 3B. In one embodiment, an ultrasonic energy source 330 is further coupled to the nanomixer 300 to enhance breakdown of the biomass. In embodiments where biofuel production is later contemplated, a sugar production device 340 is further coupled in line to the nanomixer 300. In one embodiment, a fermentation device 350 is further coupled in line with the sugar production device 340.

Figure 4A:
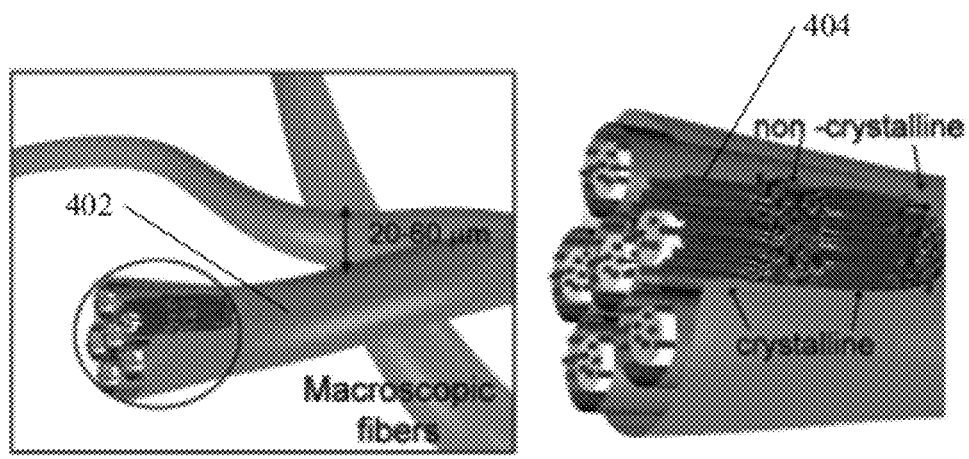
FIG. 4A shows a portion of biomass according to an embodiment.
Figure 4B:
FIG. 4B shows a portion of biomass after treatment according to an embodiment.

FIG. 4A shows an illustration of an unprocessed biomass fiber 402 (known to have a degree of crystallinity, i.e., crystallinity index (CI) of about 35 to 50, depending on type, moisture content, and the like). The magnified view in FIG. 4A shows that example unprocessed biomass fibers 402 are composed of an amount of nano-sized fragments, including nanofibrils 404 having a CI of at least about 20 and linear order. In one embodiment, an amount of microfibrils may also be present. In one embodiment, processes as described above are effective at breaking down the crystallinity and order of the biomass crystal to produce nano-sized particles, such as the nanofibrils 404 shown in FIG. 4A, such that downstream processes, such as pulp production or sugar production for biofuels, are more efficient. FIG. 4B shows an illustration of a number of nanofibrils 404 after processing according to embodiments of the invention.

FIG. 5A through 5E are scanning electron microscope images of biomass particles with varying treatments. The biomass shown includes corn stover. SEM study can provide another perspective, truly reflecting the change microscopically. The SEM images show the effectiveness of technology (fiber breakdown within about 2 min).

By combining mechanical, chemical and thermal pretreatments into a single combined in situ step as described herein, the overall process is more efficient and economical than if each pretreatment step was performed separately. As such, use of the one-step pretreatment method as described herein surprisingly provides a synergistic effect, i.e., the combination of the different types of pretreatment methods (e.g., mechanical, chemical and thermal, including making use of inherent thermal conditions) function together to produce a result not independently obtainable. In one embodiment, operating temperatures are reduced to about 25 to about 100° C. as compared to higher temperatures, such as between about 140 and about 180° C.) required in multi-step processes. In one embodiment, additionally, or alternatively, the duration of treatment is reduced by at least two orders of magnitude (e.g., 200-500 min to 2 min) as compared to the duration required in multi-step processes. Additionally or alternatively, in addition to the reduced operating temperatures, in one embodiment, other process conditions are improved as compared to conventional pretreatment methods. In one embodiment, the final product, i.e., the pretreated biomass produced as a result of the one-step process, has improved properties as compared to biomass pretreated in a conventional multi-step manner including, but not limited to improved enzyme accessibility for producing biofuels and higher purity chemicals and pulp. In one embodiment, overall costs for producing biofuels, chemicals and other products using biomass as a starting material can be reduced are reduced with use of the one-step process.

Embodiments will be further described by reference to the following examples, which are offered to further illustrate various embodiments of the present invention. It should be understood, however, that many variations and modifications may be made while remaining within the scope of the present invention.

EXAMPLE 1

Biomass examples were gold coated (EMSCOPE SC500 Sputter coater, Ashford, Kent, UK) for 3.5 minutes. All SEM images were taken using JEOL 6400V (Japan Electron Optics Laboratories, JP) with a $LaB_6$ emitter.

Method

Corn stover was locally harvested, washed and oven dried. Then it was milled with a Wiley mill No. 3 (Arthur H. Thomas Co.), passing a screen with a size of 1-2 mm. The milled corn stover was stored in cold room at 4° C.

Pretreatment

Two (2) g of stored corn stover was added into the vessel, suspended in 50 ml water or sodium hydroxide solutions at different concentrations. In one example a NaOH concentration up to 4% (1 M) was used. After the nanomixer was tightly shut, an operation time of two minutes was selected, with a maximum spinning speed 50 m/s (~18000 rpm). No external removal or addition of heat to the system was provided. The shear force generated by turbine caused the degradation of the cellulose crystallinity and generated a thermal effect simultaneously due to severe friction between turbine and the viscous biomass/solvent. At various points during the testing, the vessel temperature reached 100° C. at one atmosphere at ~45 sec. After the high shear spinning was completed, cooling water was introduced until the system temperature was brought down to 25° C. The pretreated samples were collected and provided to the washing step.

Washing

The washing step was used after the pretreatment to remove the soluble components and adjust the pH. Herein the washing was conducted via two stages in each cycle, quiescence and vacuum filtration. After 10~15 min quiescence using 1 L beaker the supernatant was filtered until some solid was seen decanted onto the filter. Depending on the NaOH concentration, the pH of homogenized suspension reached 7 with 5~7 cycles.

Composition Analysis

After the pretreated biomass sample was air dried for 3 days, its moisture content reaches equilibrium and remained about ~4%. The composition analysis was then performed to determine the cellulose and hemicellulose content. The experiment was conducted according to the standard procedure provided by National Renewable Energy Laboratory (NREL).

Table 1 shows the different dilute concentrations of NaOH up to 4%.

TABLE 1

Composition analysis of different dilute NaOH concentration up to 4%

| Condition | Glucan content (%) | Xylan content (%) | Total Lignin content (ASL + AIR %) | Balance (%) |
|---|---|---|---|---|
| Untreated corn stover | 37.6 ± 0.9 | 18.1 ± 2.1 | 19.1 ± 1.6 | 74.8 |
| Water nano-hybrid treated corn stover | 46.0 ± 0.5 | 20.3 ± 0.3 | 23.2 ± 0.6 | 89.5 |
| 0.4% NaOH nano-hybrid treated corn stover | 50.1 ± 0.3 | 21.5 ± 0.4 | 18.8 ± 2.1 | 90.4 |
| 2% NaOH nano-hybrid treated corn stover | 63.4 ± 2.0 | 15.3 ± 0.3 | 17.7 ± 2.4 | 96.4 |
| 4% NaOH nano-hybrid treated corn stover | 72.7 ± 2.2 | 9.9 ± 0.6 | 9.7 ± 1.7 | 92.3 |

Enzymatic Hydrolysis

The pretreated sample was enzymatically hydrolyzed using ACCELLEASE™ 1000 (Danisco US Inc. Genencor Div., NY, US). Under 5% solid loading, pretreated corn stover was immersed in pH 4.8 citrate buffer solution, then incubated in water bath shaker (New Brunswick Scientific Co. Inc., NJ, US) at 150 rpm, 50° C. for 168 h. The hydrolysis time of 4 h, 8 h, 12 h, 24 h, 24 h, 48 h and 72 h were selected for kinetic study. The procedure and calculation were performed as per NREL LAP 013. At least triplicate tests were performed to produce one data point. The glucose and xylose concentration were tested using High Performance Liquid Chromatography (HPLC, Agilent Technologies Inc., CA, US) with Bio-Rad ameinex HPX-87H HPLC column (Bio-Rad Laboratories, CA, US).

Figure 5A:
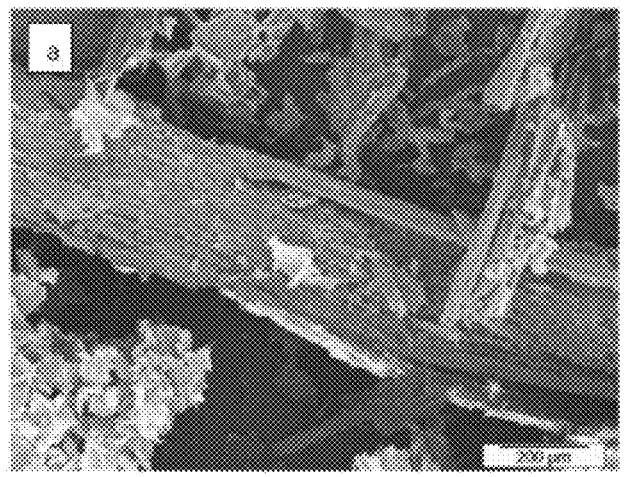
FIG. 5A shows a portion of an untreated biomass according to an embodiment.
Figure 5B:
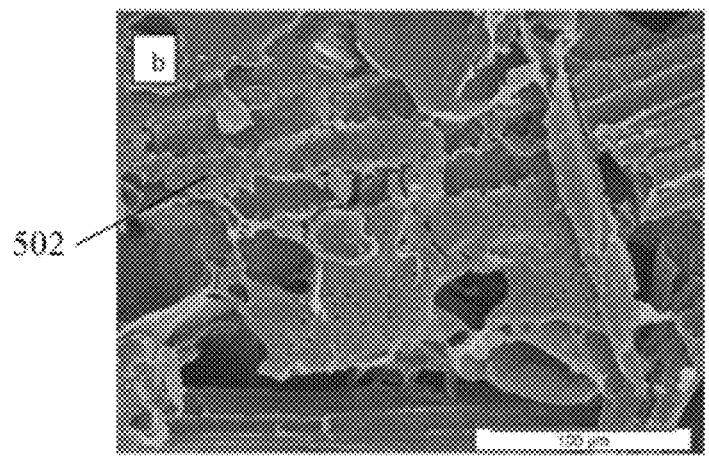
FIG. 5B shows a portion of a treated biomass according to an embodiment.
Figure 5C:
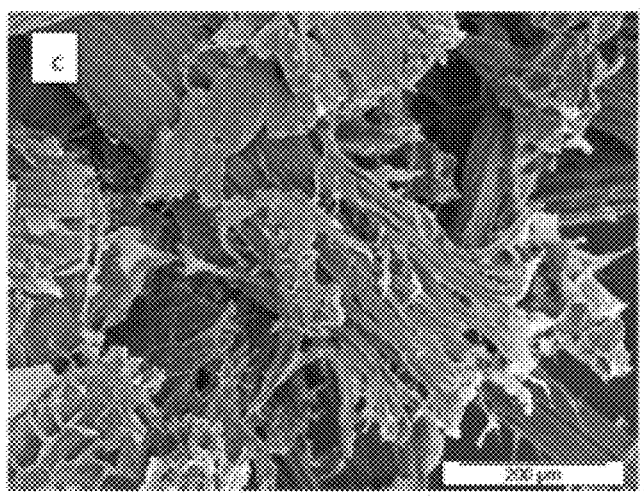
FIG. 5C shows another portion of a treated biomass according to an embodiment.
Figure 5D:
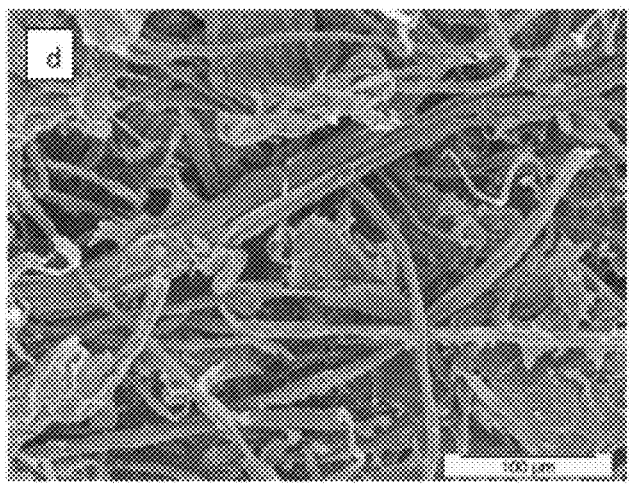
FIG. 5D shows another portion of a treated biomass according to an embodiment.
Figure 5E:
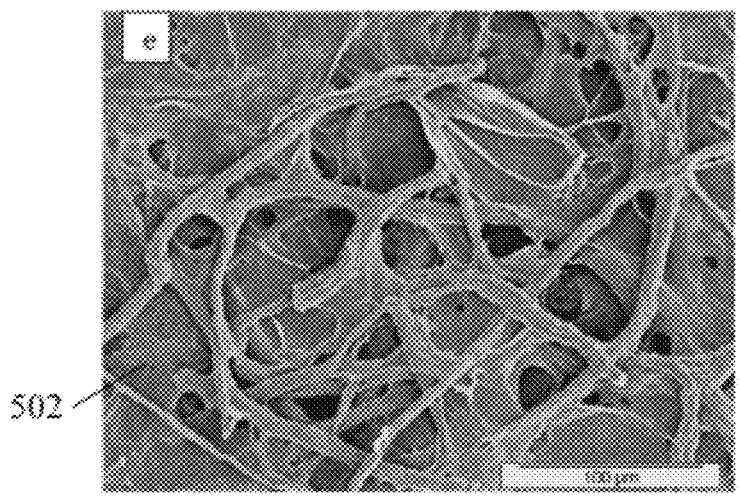
FIG. 5E shows another portion of a treated biomass according to an embodiment.

FIG. 5A shows untreated corn stover. FIG. 5B shows a water nano-hybrid treated corn stover. FIG. 5C shows a 0.4% NaOH nano-hybrid treated corn stover. FIG. 5D shows a 2% NaOH nano-hybrid treated corn stover. FIG. 5D shows a 4% NaOH nano-hybrid treated corn stover. A number of micropores 502 were visible after various treatments. In the example shown, the micropores 502 were on the order of one micron in diameter.

Figure 6A:
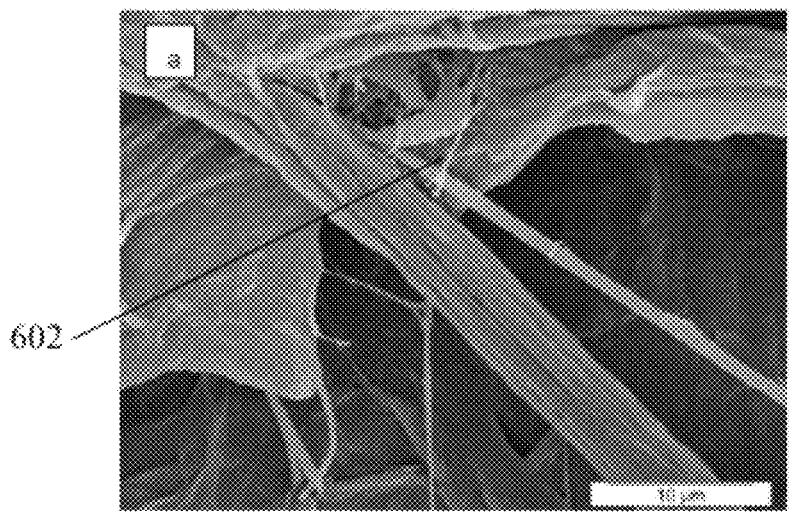
FIG. 6A shows another portion of a treated biomass according to an embodiment.
Figure 6B:
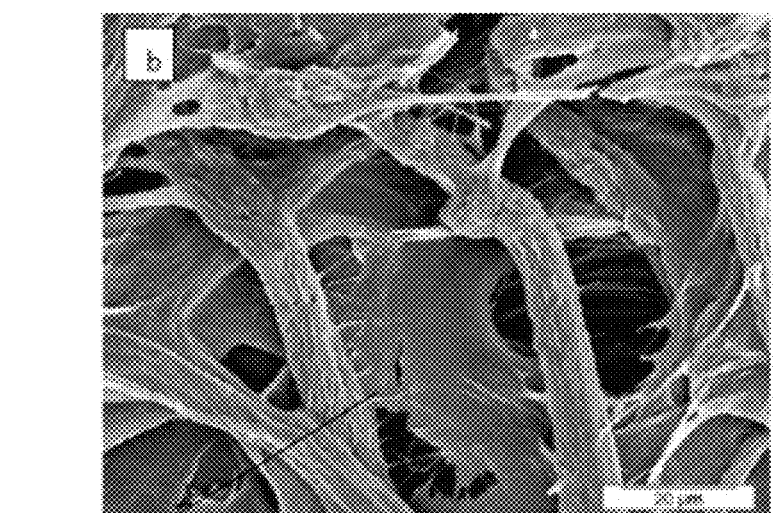
FIG. 6B shows another portion of a treated biomass according to an embodiment.

FIGS. 6A and 6B show nanofibrils that have been sheared off the cellulose crystalline structure. FIG. 6A shows a 2% NaOH nano-hybrid treated corn stover. FIG. 6B shows a 4% NaOH nano-hybrid treated corn stover. A number of nanofibrils 602 were visible after the treatments.

Conclusions

The impact of the high shear force on the biomass can be separated into two aspects. Specifically, the high shear force nanomixing itself can degrade the cellulose crystalline structure and open up micropores on the surface in an amount sufficient to improve enzymatic hydrolysis. As the results show, an alkaline fluid, such as NaOH, further improved the process, indicating that NaOH is also useful for breaking down most (i.e., >50%) of the lignin and part of the hemicelluloses.

Additionally, use of a nanomixer reduced the reaction time of NaOH as compared to known times (e.g., Mosier, supra) for conventional mixers to just few minutes (such as no more than about two (2) minutes) without requiring added heat. Furthermore, the diffusion boundary between solid-liquid phases was eliminated so that NaOH was able to react with lignin and hemicelluloses in a very short time (i.e., less than about 2 minutes). Because the cellulose-hemicellulose and cellulose-lignin linkage were interrupted in the early stage, it is expected that the high shear force could further extend its impact on the cellulose crystalline structure, as shown in FIGS. 6A and 6B.

EXAMPLE 2

Figure 7A:
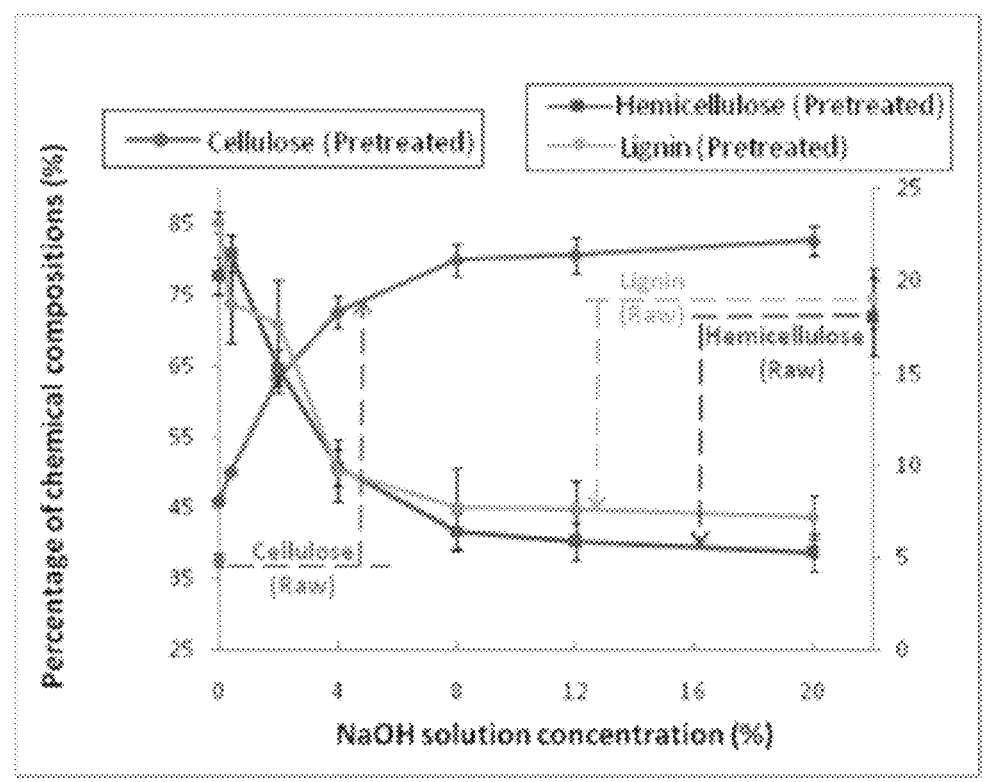
FIG. 7A shows a graph of biomass composition after treatment in various solutions according to an embodiment.

FIG. 7A shows results of Corn Stover Fiber Composition Change after 2 min Nano-hybrid Pretreatment performed according to the method described in Example 1 Values from the graph, and details of the testing procedure are shown below in Table 2.

TABLE 2

Major chemical compositions of untreated and nano-hybrid pretreated[a] corn stover at different NaOH[b] concentrations up to 20%

| Corn Stover | Chemical composition[c] (%) | | |
|---|---|---|---|
| | Cellulose | Hemicellulose | Lignin[d] |
| Untreated (Raw) | 37.6 ± 0.9 | 18.1 ± 2.1 | 19.1 ± 1.6 |
| 0% NaOH pretreated | 46.0 ± 0.5 | 20.3 ± 0.3 | 23.2 ± 0.6 |
| 0.4% NaOH pretreated | 50.1 ± 0.3 | 21.5 ± 0.4 | 18.8 ± 2.1 |
| 2% NaOH pretreated | 63.4 ± 2.0 | 15.3 ± 0.3 | 17.7 ± 2.4 |
| 4% NaOH pretreated | 72.7 ± 2.2 | 9.9 ± 0.6 | 9.7 ± 1.7 |
| 8% NaOH pretreated | 80.0 ± 2.2 | 6.4 ± 0.2 | 7.7 ± 2.2 |
| 12% NaOH pretreated | 80.7 ± 2.5 | 5.9 ± 0.1 | 7.6 ± 1.6 |
| 20% NaOH pretreated | 82.7 ± 2.0 | 5.3 ± 0.1 | 7.2 ± 1.2 |

[a]Nano-hybrid Pretreatment: 2 g corn stover samples were pretreated with 50 ml NaOH solutions in different concentrations under 50 m/s nanomixing for 2 min.
[b]The concentration of NaOH solution was calculated by weight percentage (w/v).
[c]All samples were analyzed at least three times with standard deviation (±SD) calculated.
[d]Values include acid soluble lignin and acid insoluble lignin.

Figure 7B:
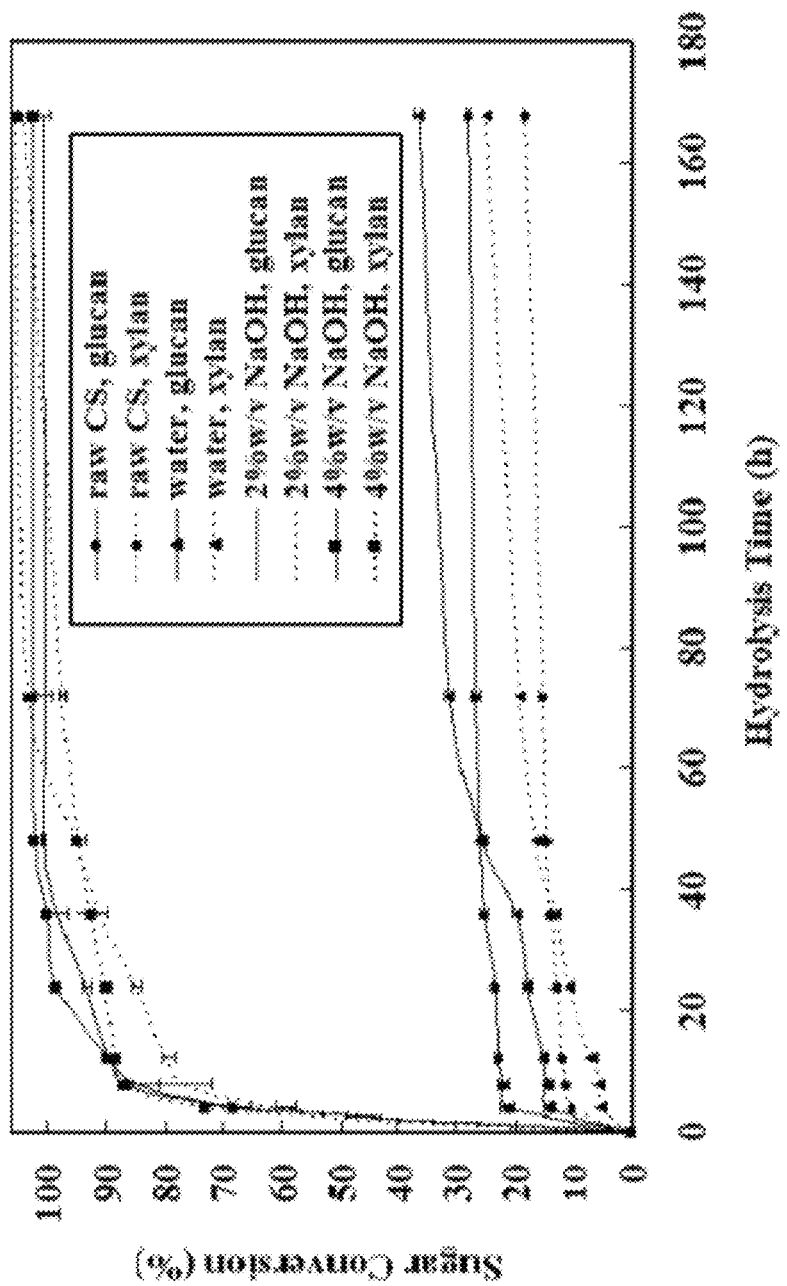
FIG. 7B shows sugar conversion of biomasses after various treatments according to an embodiment.

FIG. 7B shows results of enzymatic hydrolysis of nano-hybrid pretreated corn stovers at the various NaOH concentrations. All conditions were the same as in FIG. 7A. Tables 3 through 5 below show value calculations displayed in the graph of FIG. 7B. Note: 4% w/v NaOH pretreatment for 2 min led to very fast enzymatic hydrolysis, in which more than 98% conversion was achieved just after 1 day.

TABLE 3

Enzymatic Hydrolysis of 4% wt NaOH Nano-Hybrid Pretreated Corn Stover

| Time (h) | Calculated Cellulose conv (%) | positive Error (%) | negative Error (%) | estimated hemi conv. | positive Error (%) | negative Error (%) |
|---|---|---|---|---|---|---|
| 0 | 00 | 0.00 | 0.00 | 0.00 | 0.00 | 0.00 |
| 4 | 68.16 | 0.33 | 0.39 | 73.05 | 0.31 | 0.34 |
| 8 | 86.89 | 1.45 | 1.35 | 86.76 | 1.24 | 1.22 |
| 12 | 89.76 | 0.62 | 0.37 | 88.55 | 0.94 | 1.01 |
| 24 | 98.57 | 1.20 | 1.39 | 90.04 | 1.00 | 1.32 |
| 36 | 99.99 | 1.31 | 0.95 | 92.52 | 1.61 | 2.88 |
| 48 | 102.26 | 1.08 | 0.60 | 95.20 | 0.19 | 0.19 |
| 72 | 102.65 | 1.23 | 1.07 | 103.15 | 0.81 | 0.91 |
| 168 | 102.65 | 0.32 | 0.24 | 105.04 | 0.35 | 0.19 |

TABLE 4

Enzymatic Hydrolysis of 2% wt NaOH Nano-Hybrid Pretreated Corn Stover

| Time (h) | Calculated Cellulose conv (%) | positive Error (%) | negative Error (%) | estimated hemi conv. | positive Error (%) | negative Error (%) |
|---|---|---|---|---|---|---|
| 0 | 0.00 | 0.00 | 0.00 | 0.00 | 0.00 | 0.00 |
| 4 | 67.14 | 1.82 | 1.36 | 59.46 | 1.50 | 0.98 |
| 8 | 84.87 | 3.43 | 2.67 | 76.57 | 4.78 | 3.00 |
| 12 | 89.45 | 0.60 | 1.05 | 79.63 | 1.18 | 0.82 |
| 24 | 93.35 | 0.61 | 0.87 | 84.93 | 0.61 | 0.78 |
| 36 | 98.17 | 1.49 | 0.93 | 90.95 | 1.32 | 0.88 |
| 48 | 100.65 | 0.31 | 0.41 | 94.34 | 0.53 | 0.82 |
| 72 | 100.47 | 1.26 | 1.50 | 97.29 | 0.45 | 0.40 |
| 168 | 100.54 | 0.61 | 1.05 | 103.73 | 0.92 | 0.63 |

TABLE 5

Enzymatic Hydrolysis Unpretreated (Raw) Corn Stover

| Time (h) | Calculated Cellulose conv (%) | positive Error (%) | negative Error (%) | estimated hemi conv. | positive Error (%) | negative Error (%) |
|---|---|---|---|---|---|---|
| 0 | 0.00 | 0.00 | 0.00 | 0.00 | 0.00 | 0.00 |
| 4 | 21.37 | 1.00 | 0.91 | 10.35 | 0.45 | 0.28 |
| 8 | 22.04 | 0.69 | 0.76 | 11.60 | 0.29 | 0.38 |
| 12 | 22.97 | 0.59 | 0.60 | 12.32 | 0.26 | 0.33 |
| 24 | 23.60 | 0.24 | 0.28 | 13.18 | 0.08 | 0.07 |
| 36 | 25.25 | 0.42 | 0.57 | 13.93 | 0.13 | 0.16 |
| 48 | 25.98 | 0.29 | 0.27 | 14.69 | 0.18 | 0.18 |
| 72 | 26.87 | 0.79 | 0.73 | 15.46 | 0.34 | 0.23 |
| 168 | 28.15 | 0.42 | 0.44 | 18.39 | 0.24 | 0.27 |

EXAMPLE 3

Unless otherwise noted, testing was performed as described in the above examples. In this instance, NaOH was used as the fluid.

Figure 8A:
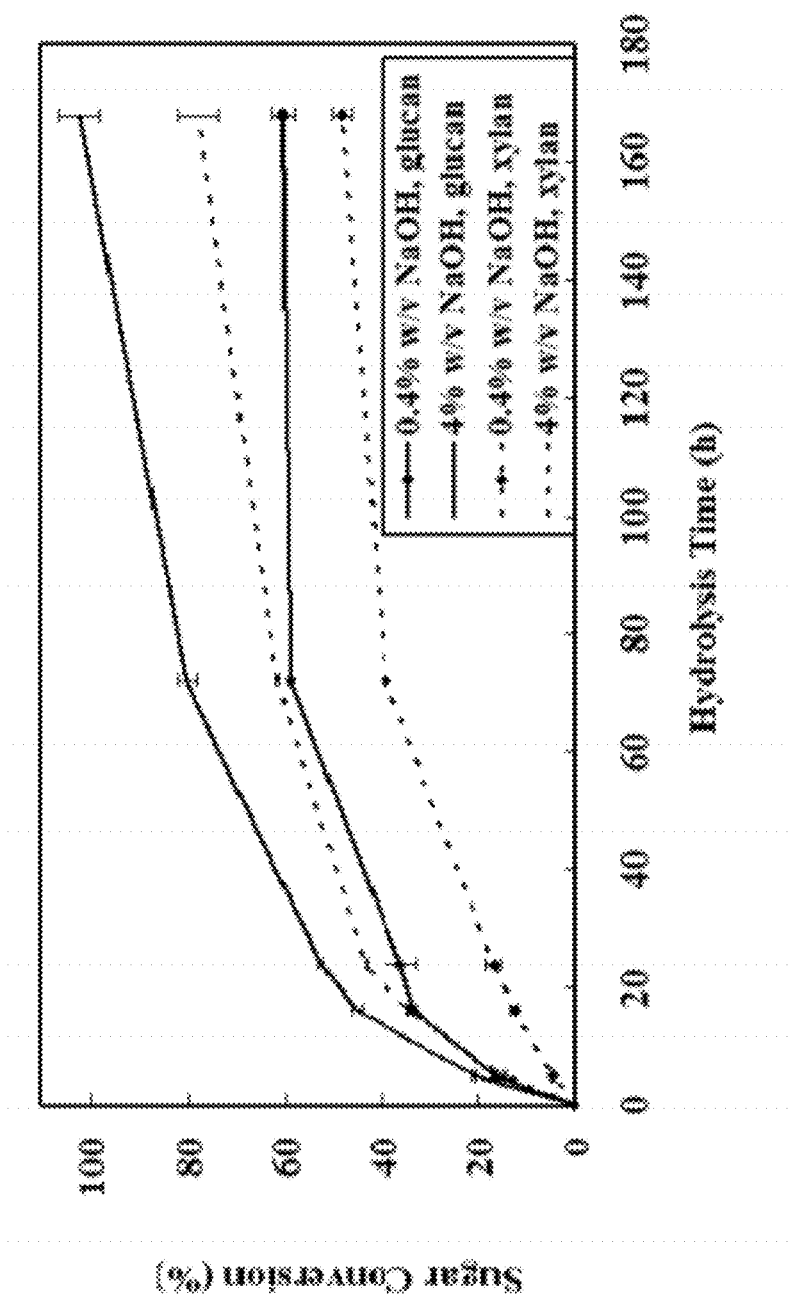
FIGS. 8A and 8B show enzymatic hydrolysis of nano-hybrid pretreated corn stovers at different enzyme loading at 0.4% w/v and 4% w/v NaOH concentrations according to various embodiments.
Figure 8B:
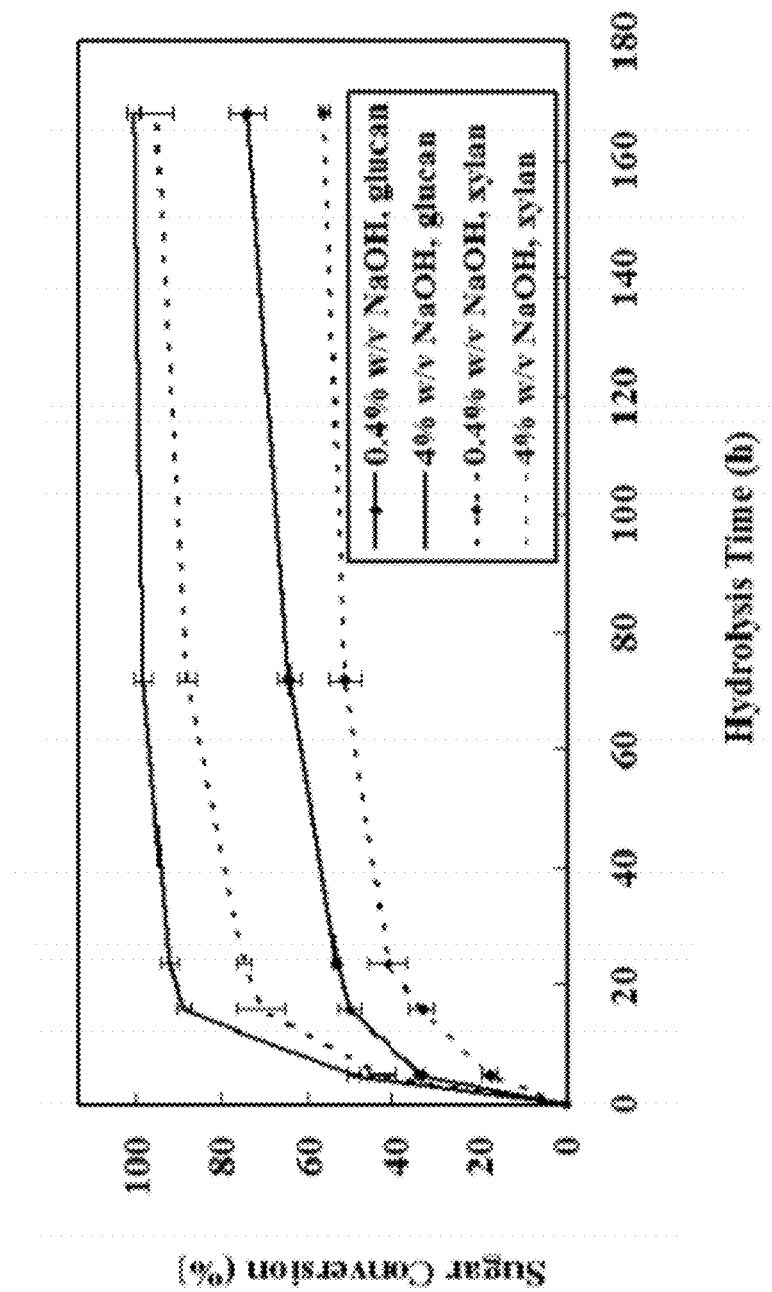

FIGS. 8A and 8B show enzymatic hydrolysis of nano-hybrid pretreated corn stovers at different enzyme loading at NaOH concentrations of 0.4% w/v and 4% w/v. Note that at 4%% w/v NaOH nano-hybrid pretreatment, the cellulose conversion was 92% in 1 day (FIG. 8B).

EXAMPLE 4

Unless otherwise noted, testing was performed as described in the above examples. In this instance, NaOH aqueous solution with and without a polyelectrolyte additive known as poly(diallyldimethylammonium chloride) (PDAC) was used as the fluid.

Figure 9A:
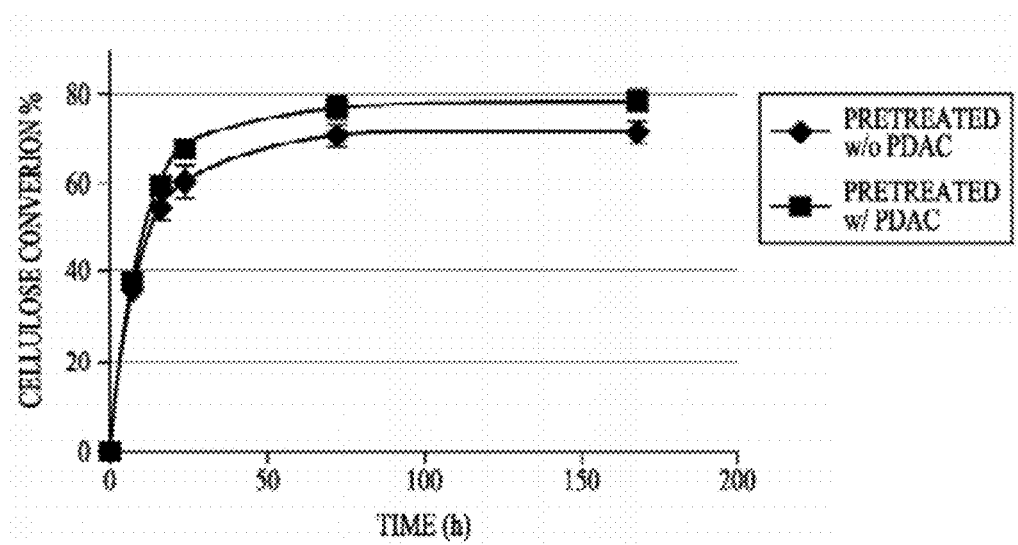
FIGS. 9A and 9B show comparisons of cellulose and hemicellulose conversions of nano-hybrid pretreated corn stovers by 0.4% w/v NaOH with/without poly(diallyldimethylammonium chloride) (PDAC) according to various embodiments.
Figure 9B:
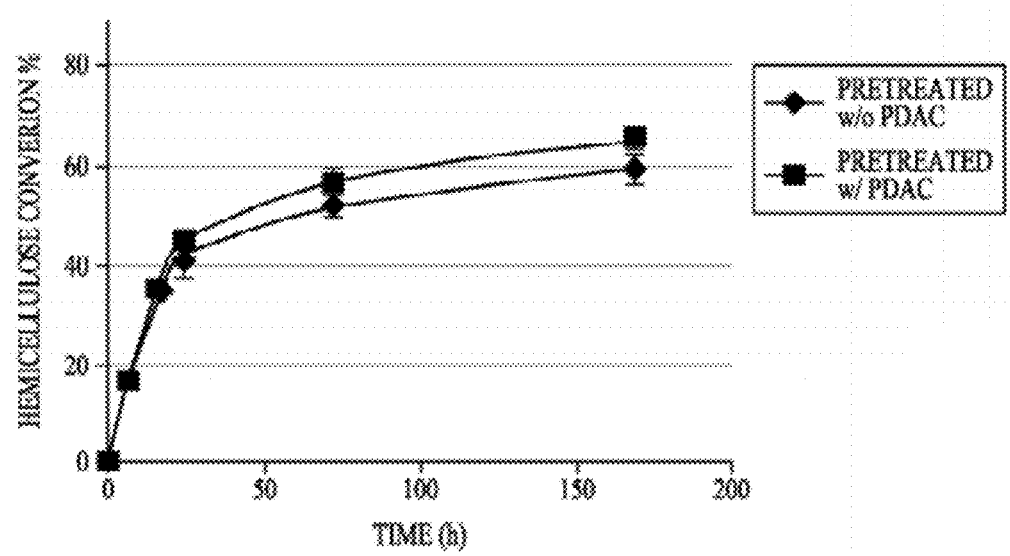

FIGS. 9A and 9B show comparisons of cellulose and hemicellulose conversions of nano-hybrid pretreated corn stovers by 0.4% w/v NaOH with/without PDAC. The concentration of PDAC (Mw≈100000-200000) was 10 mM.

With the addition of PDAC during pretreatment process, cellulose conversion was about 7% higher than the one pretreated without PDAC after 1 day hydrolysis. The enhancement of 5% can be seen in the hemicellulose conversion in FIG. 9B. Additionally, enzymatic hydrolysis was improved, which can reduce costs associated with usage of enzymes by substituting commonly available polyelectrolytes.

CONCLUSION

Methods and devices for treatment of biomass are described that include nanomixing together with chemical and thermal effects. This nano-hybrid pretreatment (i.e., hybrid nanomixing) surprisingly provides synergistic breakdown of the cell wall structures of the biomass. As such, the hybrid nanomixing provides efficient, and cost-effective breakdown which enhances enzymatic accessibility to lignocellulosic materials. In one embodiment, the process is operated continuously. Methods and devices shown can be used to produce products such as pulp, chemicals, or biofuels.

While a number of embodiments are described, the above lists are not intended to be exhaustive. Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present invention. It is to be understood that the above description is intended to be illustrative and not restrictive. Combinations of the above embodiments, and other embodiments, will be apparent to those of skill in the art upon studying the above description.

What is claimed is:

1. A method of treating biomass, comprising:
    combining an amount of biomass with an amount of fluid, wherein said biomass contains crystalline structures; and
    in a one-step process, nanomixing said biomass and said fluid in a turbine nanomixer to form a biomass slurry, wherein the nanomixing breaks down the crystalline structures and opens up pores located in the crystalline structures, wherein the open pores have a diameter of no more than 1 micron.

2. The method of claim 1, wherein the turbine nanomixer operates at turbine speeds between about 10 meters per second and about 50 meters per second.

3. The method of claim 1, wherein a mixing temperature is about 25 to about 100° C. and a mixing pressure is about one atmosphere.

4. The method of claim 1, wherein the fluid has an acidic pH.

5. The method of claim 4, wherein the fluid is selected from sulfuric acid, hydrochloric acid, nitric acid, phosphoric acid and combinations thereof.

6. The method of claim 1, wherein the fluid has a basic pH.

7. The method of claim 6, wherein the fluid is a sodium hydroxide solution.

8. The method of claim 7, wherein the biomass is corn stover.

9. The method of claim 1, wherein the fluid includes a component selected from oxygen, hydrogen peroxide, sulfur dioxide, anthraquinone (AQ), and combinations thereof.

10. The method of claim 1, wherein the fluid is an ionic liquid.

11. The method of claim 10 wherein the ionic liquid is selected from pyridinium chloride, 1-ethyl-3-methylimidazolium dicyanamide, I-butyl 3,5dimethylpyridinium bromide, and combinations thereof.

12. The method of claim 1, wherein the combining step comprises continuously flowing an amount of biomass and an amount of fluid through the processing chamber, wherein nanomixing the biomass and the fluid occurs as said biomass and said fluid flow through the processing chamber.

13. The method of claim 1, wherein the nanomixing is controlled by regulating a flow rate through the processing chamber.

14. The method of claim 1 further comprising:
    forming glucose and xylose from the biomass slurry; and
    fermenting the glucose and xylose to produce a biofuel.

15. A product made according to the method of claim 14.

16. The method of claim 1 wherein the biomass slurry is useful for product formation downstream.

17. The method of claim 16 wherein the product is a biofuel.

18. The method of claim 1 wherein the nanomixing causes at least 50% of the crystalline structures to be broken down.

19. The method of claim 1 wherein the nanomixing allows downstream processes to benefit from enhanced enzymatic accessibility to the crystalline structures.

20. The method of claim 1 wherein the single step process is performed in a period of time comprising less than 60 minutes.

21. The method of claim 20 wherein the nanomixing is hybrid nanomixing.

22. A method of treating biomass, comprising:
    combining an amount of biomass with an amount of fluid, wherein said biomass contains crystalline structures; and
    in a turbine nanomixer operating at turbine speeds from about 10 meters per second to about 50 meters per second, nanomixing said biomass and said fluid in a processing chamber to form a biomass slurry, wherein the nanomixing is performed at no less than 18,000 revolutions per minute and breaks down the crystalline structures and opens up pores located in the crystalline structures.

23. A method of treating biomass, comprising:
    combining an amount of biomass with an amount of fluid, wherein said biomass contains crystalline structures; and
    nanomixing said biomass and said fluid in a processing chamber to form a biomass slurry, wherein the nanomixing breaks down the crystalline structures and opens up pores located in the crystalline structures, wherein said fluid includes a component selected from sodium hydroxide, sodium peroxide, calcium hydroxide, aqueous ammonia, a binding agent, a surfactant, and combinations thereof, wherein the binding agent is a phenolic binding agent selected from poly(diallyldimethylammonium chloride) (PDAC), sulfonated poly(styrene) (SPS), poly(ethyleimine) (PEI), Poly(acrylic) acid (PAA), Poly(3,4-ethylenedioxythiophene) (PEDT), polyvinylpyrolidone (PVP), and combinations thereof.

24. A method of treating biomass, comprising:
    combining an amount of biomass with an amount of fluid, wherein said biomass contains crystalline structures; and
    nanomixing said biomass and said fluid in a processing chamber to form a biomass slurry, wherein the nanomixing breaks down the crystalline structures and opens up pores located in the crystalline structures, wherein said fluid includes a component selected from sodium hydroxide, sodium peroxide, calcium hydroxide, aqueous ammonia, a binding agent, a surfactant, and combinations thereof, wherein the surfactant is selected from sodium dodecylbenzene sulfonate (SDBS), sodium dodecyl sulfate (SDS), and combinations thereof.

25. The method of claim 20 wherein the period of time is from about 2 minutes to about 30 minutes.

26. The method of claim 20 wherein the period of time is from about 1.5 minutes to about 2.5 minutes.

27. The method of claim 23 wherein the open pores have a diameter ranging from about 1 to about 5 microns.

28. The method of claim 24 wherein the open pores have a diameter ranging from about 1 to about 5 microns.

* * * * *

UNITED STATES PATENT AND TRADEMARK OFFICE
CERTIFICATE OF CORRECTION

PATENT NO. : 8,741,632 B2  Page 1 of 1
APPLICATION NO. : 13/194689
DATED : June 3, 2014
INVENTOR(S) : Ilsoon Lee et al.

It is certified that error appears in the above-identified patent and that said Letters Patent is hereby corrected as shown below:

On the Title Page

Page 2/Other Publications/Col. 1/Line 19: Error reads as "Prettreated" and should read as "Pretreated"

In the Specification

Col. 3/Line 21: Error reads as "Bassicacae" and should read as "Brassicaceae"

Col. 4/Line 62-63: Error reads as "polyvinylpyrolidone" and should read as "polyvinylpyrrolidone"

Col. 5/Line 40: Error reads as "polyvinylpyrolidone" and should read as "polyvinylpyrrolidone"

Col. 10/Line 34: Error reads as "24h, 24h," and should read as "24h,"

Col. 10/Line 40: Error reads as "ameinex" and should read as "aminex"

Col. 13/Line 55: Error reads as "l-butyl 3,5dimethylpyridinium" and should read as "1-butyl-3,5-dimethylpyridinium"

In the Claims

Col. 14/Line 44: Error reads as "(PE|)," and should read as "(PEI),"

Col. 14/Line 46: Error reads as "polyvinylpyrolidone" and should read as "polyvinylpyrrolidone"

Signed and Sealed this
Twenty-sixth Day of August, 2014

Michelle K. Lee
*Deputy Director of the United States Patent and Trademark Office*